United States Patent
Tomer et al.

US 6,465,017 B1

(10) Patent No.: US 6,465,017 B1
(45) Date of Patent: Oct. 15, 2002

(54) PROCESS FOR THE PREPARATION OF SOLID ORAL DOSAGE FORMS COMPRISING ALENDRONIC ACID

(75) Inventors: Zevulun Tomer; Ron Tomer, both of Tel-Aviv (IL)

(73) Assignee: Unipharm Ltd., Tel-Aviv (IL)

(*) Notice: Subject to any disclaimer, the term of this patent is extended or adjusted under 35 U.S.C. 154(b) by 0 days.

(21) Appl. No.: 09/486,425

(22) PCT Filed: Aug. 18, 1998

(86) PCT No.: PCT/IL98/00389

§ 371 (c)(1),
(2), (4) Date: Feb. 25, 2000

(87) PCT Pub. No.: WO99/09995

PCT Pub. Date: Mar. 4, 1999

(30) Foreign Application Priority Data

Aug. 26, 1997 (IL) .................................................. 121623

(51) Int. Cl.⁷ .............................. A61K 9/16; A61K 9/20; A61K 9/48
(52) U.S. Cl. ........................ 424/499; 424/501; 424/451; 424/464
(58) Field of Search ................................. 424/468–470, 424/458, 461–462, 451, 494–495, 464, 499, 501, 486, 488

(56) References Cited

FOREIGN PATENT DOCUMENTS

| WO | WO 94/12200 | 6/1994 | .......... A61K/31/66 |
|---|---|---|---|
| WO | WO 95/08331 | 3/1995 | .......... A61K/31/66 |
| WO | WO 95/29678 | 11/1995 | .......... A61K/31/55 |
| WO | WO 95/29679 | 11/1995 | .......... A61K/31/66 |
| WO | WO 97/12620 | 4/1997 | .......... A61K/31/675 |
| WO | WO 97/44017 | 11/1997 | ............ A61K/9/46 |

OTHER PUBLICATIONS

International Search Report, PCT/II98/00389.

*Primary Examiner*—Edward J. Webman
(74) *Attorney, Agent, or Firm*—Myers Bigel Sibley & Sajovec, P.A.

(57) ABSTRACT

The present invention relates to a process for preparing solid oral dosage forms e.g. tablets, capsules, coated tablets/capsules, etc. comprising as active ingredient 4-amino-1-hydroxybutylidene-1, 1-biphosphonic acid or one of its pharmaceutically acceptable salts ("Alendronic acid"). It comprises the free acid or one of its pharmaceutically acceptable salts. The process is characterized by granulating pharmaceutical carriers with an aqueous solution of Alendronic acid which is solubilized with the aid of alkaline hydroxides or alkaline salts. The oral dosage forms obtained by this process are less irritating to the digestive system than oral dosage forms obtained by conventional processes. The present invention also relates to tablets and to capsules prepared by said process.

21 Claims, No Drawings

PROCESS FOR THE PREPARATION OF SOLID ORAL DOSAGE FORMS COMPRISING ALENDRONIC ACID

RELAYED APPLICATION INFORMATION

This application claims priority under 35 U.S.C. §371 from PCT Application No. PCT/IL98/00389, filed on Aug. 18, 1998, the disclosure of which is incorporated by reference herein in its entirety, which claims priority from Israeli Application No. 121623, filed on Aug. 26, 1997, the disclosure of which is incorporated by reference herein in its entirety.

FIELD OF THE INVENTION

The present invention generally relates to pharmaceutically active compositions and methods of making the same.

The present invention relates to a process for the preparation of solid oral dosage forms such as tablets, capsules, granules,etc comprising as active ingredient 4-amino-1-hydroxybutylidene-1,1-biphosphonic acid or one of its pharmaceutical acceptable salts in particular the sodium or potassium salts. (Said acid will be called hereinafter "Alendronic acid". It comprises unless otherwise stated the free acid or one of its pharmaceutically acceptable salts.)

Alendronic acid is a known compound. It serves for the treatment of diseases abnormal (ectopic) depositions of calcium salts and in the reduction of bone resorption. As such diseases there may be mentioned, inter alia, osteoporosis, menopausal osteoporosis, osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, sclerosis, arthritis, bursitis, neuritis and tetany.

There are known various processes for the preparation of tablets comprising as active ingredient alendronic acid, for example, from the following patent Specifications:
1. WO/94/12200 which describes and claims the preparation of such tablets by a dry method;
2. WO/95/29679 which describes and claims the preparation of such tablets by wet granulation; and
3. WO/95/08331 which describes and claims the preparation of such tablets coated by an enteric coat.

In the wet granulation process described and claimed in WO/95/29679 all ingredients including the Alendronic acid are admixed and the mixture is wetted with water, an organic solvent or a solution of said solvent in water.

However,the tablets obtained by said processes are not entirely satisfactory in particular the processes described in 1. and 2. The tablets obtained by said processes irritate to an undesired extent the digestive system; and the absorption of the alendronic acid is not entirely satisfactory.

It has thus been desirable to develop a process which provides tablets which cause less irritation to the digestive system; and in which the absorption of the alendronic acid is improved.

The present invention thus consists in a process for the preparation of tablets or capsules comprising as active ingredient alendronic acid (as herein defined) comprising:
1. forming a powder blend of inert pharmaceutically acceptable excipients;
2. granulation of the powder with a suitable aqueous solution containing alendronic acid;
3. drying the granules obtained; and, if desired,
4. either compressing the granulate obtained into tablets; or filling same into capsules.

In an optional step a binder, is added to the powder blend prepared in step 1 and/or to the wetting solution obtained in step 2. As binder, if any, there may be used, e.g. polyvinylpyrrolidone (PVP), hydroxypropylmethylcellulose (HPMC), pregelatinized starch, etc.

The excipients used in step 1 are carriers, e.g. microcrystalline cellulose, lactose, calcium hydrogen phosphate, calcium triphosphate, etc. advantageously admixed with disintegrants, e.g. carboxymethylcellulose sodium (croscarmellose sodium), sodium carboxymethylstarch (Primojel®), crospovidone, etc. There may be used one or more carriers and one or more disintegrants.

The aqueous solution used in step 2 is preferably prepared by admixing the alendronic acid with an alkali advantageously NaOH, KOH, $NH_4OH$, etc, in a ratio of 1 : 1–4 moles, preferably 1 : 1–3 moles.

However, said aqueous solution may be prepared also by other suitable methods, e.g. by admixing the alendronic acid with a salt of a weak acid and a strong base; or by admixing the alendronic acid with any suitable water soluble salt enabling to solubilize the alendronic acid. All the various reagents should be pharmaceutically acceptable.

The method according to the present invention differs from that of WO/95/29679 as specified above in that the alendronic acid is dissolved in water and said solution is used for the granulation of the powder blend.

The ratio between the power blend obtained in step 1 and the solution used in step 2 is preferably 1 : 0.2 to 1 : 4. In case that the amount of the solution used in step 2 is large the addition of the solution to the powder is done in portions, and the granules are dried after the addition of each portion.

The drying step is suitably performed in a tray oven, preferably in a fluid bed advantageously at an inlet temperature of about 50° C.

The dried granulates obtained are preferably sieved, advantageously with a mesh 16 sieve.

The dried granules obtained are advantageously, preferably after sieving, admixed with lubricants and/or with disintegrants. Some more of the carriers used in step 1 may be added to the dry granules. Said disintegrants may be the same as those used in step 1. The lubricants may be, e.g. magnesium stearate, calcium stearate, sodium lauryl sulfate, etc. The quantity of the various lubricants and/or the disintegrants is preferably 0.1 to 5% of the granule weight.

All said carriers, disintegrants and lubricants should be pharmaceutically acceptable.

The present invention also consists in a tablet prepared by the method according to the present invention. Said tablet weighs, e.g. 40–1200 mg and comprises, e.g. 1–25%, advantageously 2–15% of the alendronic acid.

The present invention also consists in a capsule comprising granules as prepared by the process according to the present invention.

The tablets and the capsules may be entero-coated by known conventional techniques with solutions or suspensions of suitable polymers used for entero-coating, e.g. of cellulose acetate phthalate (CAP), hydroxypropyl methylcellulose phthalate (HPMCP), Eudragit L®, etc. Said solutions and suspensions may comprise additional compounds used for film coating.

A subcoat formed from an inert water soluble polymer, e.g. hydroxypropylmethylcellulose (HPMC), hydroxypropylcellulose (HPC), povidone (PVP), etc. may be applied between the tablets and/or capsules and the entero-coat outer layer.

The present invention will now be illustrated with reference to the Examples without being restricted by them.

EXAMPLE 1

Preparation of the Granulation Wetting Solution containing the

Alendronic Acid and a binder 42.75 g of Alendronic Acid Monohydrate was dissolved in 1,200 ml of an aqueous solution containing 6.5 g of Sodium Hydroxide and 24 g of PVP.

Preparation of the Powder Mixture 600 g of Lactose, 395 g of Microcrystalline Cellulose and 5 g of Croscarmellose Sodium were passed through a 30 mesh screen and mixed in a fluid bed granulator.

Granulation Step

The granulation wetting solution was sprayed on the powder mixture in a fluid bed granulator to obtain a granulate which was then dried in the fluid granulator at an inlet temperature of 50° C.

Preparation of the Granulate for Tabletting

The dried granulate was passed through a 16 mesh sieve and mixed in a drum mixer with 5 g of Croscarmellose Sodium and 10 g of Magnesium Stearate.

Preparation of Tablets

The granulate was compressed into tablets, each containing an equivalent to 10 mg of Alendronic Acid. The average weight of the tablets was 275 mg.

EXAMPLE 2

Preparation of the Granulation Wetting Solution Containing Alendronic Acid and a Binder 85.5 g of Alendronic Acid Monohydrate was dissolved in 700 ml of an aqueous solution containing 36 g of Potassium Hydroxide.

Preparation of the Powder Mixture 550 g of Calcium Hydrogen Phosphate Dihydrate, 400 g of Corn Starch, 900 g of Microcrystalline Cellulose, 135 g of Pregelatinized Starch and 15 g of Crospovidone were passed through a 30 mesh screen and mixed in a fluid bed granulator.

Granulation Step

The granulation wetting solution was sprayed on the powder mixture in a fluid bed granulator to obtain a granulate which was then dried in the fluid bed granulator at an inlet temperature of 50° C.

Preparation of the Granulate for Tabletting

The dried granulate was passed through a 16 mesh sieve and mixed in a drum mixer with 15 g of Crospovidone and 22 g of Magnesium Stearate.

PreDaration of Tablets

The granulate was compressed into tablets, each containing an equivalent to 10 mg of Alendronic Acid. The average weight of the tablets was 270 mg.

EXAMPLE 3

Preparation of the Granulation Wetting Solution Containing Alendronic Acid and a Binder 85.5 g of Alendronic Acid Monohydrate was dissolved in 1000 ml of an aqueous solution containing 26 g of Sodium Hydroxide and 140 g of Pregelatinized Starch.

Preparation of the Powder Mixture 350 g of Tricalcium Phosphate, 450 g of Corn Starch, 105 g of Microcrystalline Cellulose and 20 g of Crospovidone were passed through a 30 mesh screen and mixed in a fluid bed granulator.

Granulation Step

The granulation wetting solution was sprayed on the powder mixture in a fluid bed granulator to obtain a granulate which was then dried in the fluid bed granulator at an inlet temperature of 50° C.

Preparation of the Granulate for Tabletting

The dried granulate was passed through a 16 mesh sieve and mixed in a drum mixer with 20 g of Crospovidone and 20 g of Magnesium Stearate.

Preparation of Tablets

The granulate was compressed into tablets, each containing an equivalent to 10 mg of Alendronic Acid. The average weight of the tablet was 270 mg.

EXAMPLE 4

Preparation of the Granulation Wetting Solution Containing Alendronic Acid.

85.5 g of Alendronic Acid Monohydrate was dissolved in 700 ml of an aqueous solution containing 36 g of Potassium Hydroxide.

Preparation of the Powder Mixture 550 g of Calcium Hydrogen Phosphate Dihydrate, 400 g of Corn Starch, 900 g of Microcrystalline Cellulose, 135 g of Pregelatinized Starch and 15 g of Crospovidone were passed through a 30 mesh screen and mixed in a fluid bed granulator.

Granulation Step

The granulation wetting solution was sprayed on the powder mixture in a fluid bed granulator to obtain a granulate which was then dried in the fluid bed granulator at an inlet temperature of 50° C.

Preparation of Granulate for Encapsulation

The dried granulate was passed through a 16 mesh sieve and mixed in a drum mixer with 4 g of Magnesium Stearate.

Filling of Capsules

Capsules No. 3 were filled with an average of 133 mg of the granulate obtained in the previous step. Each such capsule contains an equivalent for 5 mg of Alendronic Acid.

EXAMPLE 5

Preparation of the Granulation Wetting Solution Containing Monosodium Alendronic Acid Trihydrate and a Binder 52.5 g of Monosodium Alendronic Acid Trihydrate was dissolved in 1,400 ml of an aqueous solution containing 6.5 g of Sodium Hydroxide and 24 g of PVP.

Preparation of the Powder Mixture 625 g of Lactose, 375 g of Microcrystalline Cellulose and 5 g of Croscarmellose Sodium were passed through a 30 mesh screen and mixed in a fluid bed granulator.

Granulation Step

The granulation wetting solution was sprayed on the powder mixture in a fluid bed granulator to obtain a granulate which was then dried in the fluid granulator at an inlet temperature of 50° C.

Preparation of the Granulate for Tabletting

The dried granulate was passed through a 16 mesh sieve and mixed in a drum mixer with 5 g of Croscarmellose Sodium and 10 g of Magnesium Stearate.

Preparation of Tablets

The granulate was compressed into tablets, each containing 13.125 mg of Monosodium Alendronic Acid Trihydrate equivalent to 10 mg of Alendronic Acid. The average weight of the tablets was 275 mg.

What is claimed is:

1. A process for the preparation of tablets comprising as an active ingredient alendronic acid comprising the steps of:
   (a) forming a powder blend of inert pharmaceutical excipients;
   (b) granulation of the powder with an aqueous solution comprising alendronic acid; and
   (c) drying the granules to obtain a granulate.

2. The process of claim 1, further comprising the step of compressing the granulate obtained into tablets.

3. The process of claim 1, further comprising the step of filling the granulate obtained into capsules.

4. The process of claim 1, wherein a binder is added during said forming or said granulation step.

5. The process of claim 4, wherein the binder is selected from the group consisting of polyvinylpyrrolidone, hydroxypropylmethylcellulose, hydroxypropylcellulose, pregelatinized starch, and combinations thereof.

6. The process of claim 1, wherein the excipient is a carrier.

7. The process of claim 6, wherein the carrier is selected from the group consisting of micro crystalline cellulose, lactose, calcium hydrogen phosphate, tricalcium phosphate, and combinations thereof.

8. The process of claim 6, wherein the carrier is admixed with a disintegrant.

9. The process according to claim 8, wherein the disintegrant is selected from the group consisting of carboxymethyl cellulose sodium (croscarmellose sodium), Primojel®, crospovidone, and combinations thereof.

10. The process according to claim 1, wherein the aqueous solution is prepared by admixing the alendronic acid with an alkali.

11. The process according to claim 10, wherein the alkali is selected from the group consisting of NaOH, KOH, NH$_4$OH, and combinations thereof, and the ratio between the alendronic acid and the alkali is about 1:1 to about 1:4 moles.

12. The process of claim 10, wherein the aqueous solution is prepared by admixing the alendronic acid with a salt of a weak acid and a strong base.

13. The process of claim 1, wherein said drying step is performed in a fluid bed at an inlet temperature of about 50° C.

14. The process of claim 1, wherein said granulation and drying steps are performed by adding several portions of the aqueous solution to the powder, and drying the granules obtained after each portion.

15. The process of claim 1, wherein the wherein the dried granules are sieved.

16. The process of claim 1, wherein the dried granules are admixed with lubricants.

17. The process of claim 16, wherein the lubricant is selected from the group consisting of magnesium stearate, calcium stearate, sodium lauryl sulfate, and combinations thereof.

18. The process of claim 16, wherein the quantity of the lubricant is about 0.1% to about 5% of the weight of the granules.

19. The process of claim 1, wherein the dried granules are admixed with disintegrants.

20. The process of claim 19, wherein the distintegrant is selected from the group consisting of carboxymethyl cellulose sodium (croscarmellose sodium), Primojel®, crospovidone, and combinations thereof.

21. The process of claim 19, wherein the quantity of the disintegrant is about 0.1 to about 5% of the weight of the granules.

* * * * *

UNITED STATES PATENT AND TRADEMARK OFFICE
CERTIFICATE OF CORRECTION

PATENT NO.    : 6,465,017 B1
DATED         : October 15, 2002
INVENTOR(S)   : Zevulun Tomer and Ron Tomer It is certified that error appears in the above-identified patent and that said Letters Patent is hereby corrected as shown below:

Title page,
Item [56], References Cited, OTHER PUBLICATIONS, should read as follows:
-- International Search Report PCT/IL98/00389 --

Column 1,
Line 5, should read -- RELATED APPLICATION INFORMATION --

Column 2,
Line 63, should read -- containing the Alendronic Acid and a binder --

Column 3,
Line 52, should read -- Preparation of Tablets --

Column 6,
Line 22, should read -- 15. The process of claim 1. wherein the dried --

Signed and Sealed this

Third Day of June, 2003

JAMES E. ROGAN
*Director of the United States Patent and Trademark Office*